US005235969A

United States Patent [19]

Bellm

[11] Patent Number: 5,235,969

[45] Date of Patent: Aug. 17, 1993

[54] NEBULIZER HAVING COMBINED STRUCTURE FOR REMOVING PARTICLES OVER TWO MICRONS

[75] Inventor: Howard G. Bellm, Berks, Great Britain

[73] Assignee: Intersurgical (Guernsey) Limited, England

[21] Appl. No.: 674,679

[22] Filed: Mar. 22, 1991

Related U.S. Application Data

[63] Continuation of Ser. No. 569,520, Aug. 20, 1990, abandoned.

[30] Foreign Application Priority Data

Feb. 28, 1991 [GB] United Kingdom ................. 9104199

[51] Int. Cl.[5] ........................ A61M 11/06; B05B 1/26

[52] U.S. Cl. .......................... 128/200.18; 128/200.21; 239/338

[58] Field of Search ...................... 128/200.14, 200.18, 128/200.21, 203.12; 239/338

[56] References Cited

U.S. PATENT DOCUMENTS

| | | | |
|---|---|---|---|
| 2,266,704 | 12/1941 | Fox et al. | 128/200.14 |
| 2,266,705 | 12/1941 | Fox et al. . | |
| 2,993,652 | 7/1961 | Curry . | |
| 3,097,645 | 7/1963 | Lester | 128/200.14 |
| 3,172,406 | 3/1965 | Bird et al. . | |
| 3,658,059 | 4/1972 | Steil | 128/200.14 |
| 3,826,255 | 7/1974 | Havstad et al. | 239/338 |
| 3,999,713 | 12/1976 | Lindsey | 239/426 |
| 4,333,450 | 6/1982 | Lester | 128/200.14 |
| 4,446,863 | 5/1984 | Rubin et al. | 128/204.18 |
| 4,512,341 | 4/1985 | Lester | 128/200.21 |
| 4,588,129 | 5/1986 | Shanks | 239/338 |
| 4,598,704 | 7/1986 | Bordoni et al. | 128/200.14 |
| 4,674,491 | 6/1987 | Brugger et al. | 128/200.14 |
| 4,746,067 | 5/1988 | Swoboda | 239/338 |

FOREIGN PATENT DOCUMENTS

| | | |
|---|---|---|
| 1046264 | 6/1953 | Fed. Rep. of Germany . |
| 2133377 | 1/1973 | Fed. Rep. of Germany . |
| 8437274 | 12/1984 | Fed. Rep. of Germany . |
| 686006 | 1/1953 | United Kingdom . |
| 2132508 | 7/1984 | United Kingdom . |

*Primary Examiner*—Edgar S. Burr
*Assistant Examiner*—Kimberly L. Asher
*Attorney, Agent, or Firm*—Andrus, Sceales, Starke & Sawall

[57] ABSTRACT

A nebulizer for introducing a liquid in fine droplet form into a gas flow, including a reservoir for the liquid, a side wall, a base wall of generally conical shape, the base wall extending from a lower outer periphery adjacent said side wall to a central raised part, the base wall being covered by a flange plate whereby there is provided a capillary path from the lower outer periphery to a centrally mounted jet.

15 Claims, 14 Drawing Sheets

NEBULIZER HAVING COMBINED STRUCTURE FOR REMOVING PARTICLES OVER TWO MICRONS

This application is a continuation of Ser. No. 07/569,520 filed Aug. 20, 1990, now abandoned.

The present invention relates to nebulizers. Nebulizers are used to produce a liquid in fine droplet form in a gas flow, typically a liquid in the form of medication which is to be entrained in an air or oxygen gas flow and which is then breathed by a patient whereby the medication is applied to the patient through the lungs.

Nebulizers have become widely used in hospitals and other medical situations.

Such nebulizers have a particular application in delivery of drugs for the treatment of lung diseases. Thus the drug may be given as an inhaled drug aerosol, and this has many advantages over drugs which are taken systemically. Thus the onset of the drug action is quicker, the therapeutic dose is lower, which reduces the side effects, and the drug delivery may be more selective.

It has become more widely accepted that different clinical needs require the nebulized drug to be targeted to specific areas of the lungs. Many factors can affect where the aerosol is deposited and the depth of penetration, including the patient's condition and breathing pattern. However, research has clearly shown that aerosol droplet size plays an important rôle in the area of deposition, that is the part of the lung in which the drug is deposited. To ensure that the drug is delivered to the correct part of the lung the correct droplet size must be provided.

The applicants have tested many widely available nebulizers and find that as a general rule, they provide a mass median diameter (MMD) which prevents the drug or, at least, much of the drug passing through to the alveoli.

It is therefore desirable to provide a nebulizer which produces the desired droplet sizes, in the range 0.5–8 micron, preferably 0.5–2.5 micron for deposition in the alveoli, and 2–6 micron for deposition in the tracheobronchiole area of the lung.

As an example of the use of this aspect of the invention, the ability to deliver a drug to the alveoli of the lungs can be particularly important in treating diseases of the lungs in immuno-compromised patients with pneumocystis pneumonia. The *pneumocystis carinii* protozoa can be treated by administering Pentamidine, but a particular difficulty is the toxicity of the drug. If one were able to administer Pentamidine in aerosol form of such a droplet size that the droplets were able to pass through directly to the alveoli and there be deposited, then the quantity of drug applied could be reduced considerably and this would reduce the side effects of the drug, whilst improving its efficacy.

There can be, however, a number of further problems. The nebulizer includes a reservoir for the liquid (generally water) and because of the dexterity required it is sometimes difficult for an elderly person to fill the reservoir with the required accurate quantity of water or to take the nebulizer apart for cleaning. Furthermore nebulizers tend to be quite long, and in addition, problems have been found whereby the connection of an oxygen tube to the nebulizer and movements of the patient have caused the jet arrangement within the nebulizer to become misaligned and not function properly. The usual nebulizer also includes a cap which is screwed onto the base part. The use of screw threads is inconvenient, particularly for less dextrous elderly people.

It would, therefore, be desirable to provide a compact more useful design of nebulizer which mitigates or overcomes one of more of the above problems.

The present invention provides a nebulizer comprising:

a base part including a base wall extending to an apex;
a gas input including an input connector;
a gas jet hole extending through the base wall connecting with the interior of the input connector;
a gas/liquid output;
a flange plate extending above said base wall over the gas jet hole, the under surface of said flange plate generally matching the upper surface of the base wall and being spaced from said base wall by a sufficiently small distance to provide a capillary path;
a reservoir for liquid being provided by said base wall communicating with said capillary path; and,
a gas/liquid mixing jet for mixing gas from the gas jet hole through the base wall with liquid from the capillary path, the gas/liquid mixing jet comprising a hole through the flange plate opposite and in axial alignment with said gas jet hole through the base wall;
an annular baffle plate, including a target centrally mounted on said annular baffle plate opposite said gas/liquid mixing jet against which the gas/liquid jet formed by the gas/liquid mixing jet impinges to nebulize the liquid; a ring member positioned so as, in use, to extend downwardly from the surface of the annular baffle plate, and being generally coaxial with the target, and,
outlet aperture means adjacent the outer peripheral edge of said baffle plate for allowing direct passage of the nebulized gas/liquid mixture from the nebulizer.

Preferably the lower most edge of the ring means extends below the lower most point of the target.

Preferably the target is semispherical.

Preferably the radius of the target is 2–5 mm, preferably substantially 3.5 mm.

Preferably the diameter of the ring means is 15–25 mm, preferably approximately 20 mm diameter.

Preferably the depth of the cross section of the ring means is 1–5 mm, preferably 1.5 mm.

Preferably the depth of the cross section of the ring means is approximately 3 mm.

Preferably the target comprises a conical member.

Preferably the angle of the surface of the conical target with respect to its axis is between 55 degrees and 80 degrees.

Preferably the angle of the surface of the conical target with respect to its axis is approximately 70 degrees.

Preferably the ring means is mounted by leg means, to the flange plate.

The present invention also provides a neubulizer comprising:

a reservoir for liquid to be nebulized;
a gas input including an input connector;
jet means for mixing said gas and said liquid;
a gas/liquid output;
the arrangement being such that said nebulizer provides nebulized droplets of a mass median diameter (MMD) of less than approximately 1.5 micron.

Preferably the droplet has a mass median diameter (MMD) of less than approximately 1.5 micron.

The present invention also provides a nebulizer comprising:

a base part including an outer wall and a conical base wall formed integrally with and extending smoothly and uninterruptedly from the outer wall to an apex, the upper surface of said base wall having a convex central portion including the apex;

a gas input including an input connector extending coaxially from an under surface of the conical base wall and a gas get hole through the apex of the conical base wall connecting with the interior of the input connector;

a gas/liquid output;

a flange plate extending above said conical wall from adjacent the outer periphery of the conical base wall to the apex, the under surface of said flange plate generally matching the upper surface of the base wall and being spaced from said conical base wall by a sufficiently small distance to provide a capillary path from its outer periphery to the apex;

a reservoir for liquid being provided between said flange plate and said outer wall; and, a gas/liquid mixing jet for mixing gas from the gas jet hole through the conical base wall with liquid from the capillary path, the gas/liquid jet comprising a hole through the flange plate opposite and in axial alignment with said gas jet hole through the conical base wall;

a substantially flat annular baffle plate, including a target centrally mounted on said plate opposite said gas/liquid jet against which said gas/liquid jet impinges to nebulize the liquid;

the baffle plate intersecting the periphery of the target to provide a relatively smooth transition surface in the path of movement of the nebulized gas/liquid mixture; and, outlet aperture means adjacent the outer peripheral edge of said baffle plate for allowing direct passage of the nebulized gas/liquid mixture from the nebulizer.

The present invention also provides a nebulizer comprising:

a base part comprising an outer wall and a conical base wall formed integrally with and extending smoothly and uninterruptedly from the outer wall and including an apex, said conical base wall having a convex central part on its upper surface including the apex;

a gas input comprising an input connector extending coaxially from an under surface of the conical base wall and a gas jet hole through the apex of the conical base wall connecting with the interior of the input connector;

a flange plate extending over said conical wall from adjacent the outer periphery of the conical base wall to the apex, the under surface of said flange plate generally matching the upper surface of the base wall and being spaced from said conical base wall by a sufficiently small distance to provide a capillary path from its lower outer periphery to the apex;

a reservoir for liquid being provided between said flange plate and said outer wall;

a gas/liquid mixing jet for mixing gas from the gas jet hole through the conical base wall with liquid from the capillary path, the gas/liquid jet being situated adjacent the apex of the conical base wall and comprising a hole through the flange plate opposite said gas jet hole through the conical base wall through which the gas/liquid mixture may pass;

a substantially flat annular baffle plate, including a target centrally mounted on said plate opposite said gas/liquid jet against which jet of gas/liquid impinges to nebulize the liquid;

the baffle plate intersecting the periphery of the target to provide a relatively smooth transition surface in the path of movement of the nebulized gas/liquid mixture; and, outlet aperture means adjacent the outer peripheral edge of said baffle plate for allowing direct passage of the nebulized gas/liquid mixture from the nebulizer.

The present invention also provides a nebulizer comprising:

a base part including an outer wall and a conical base wall formed integrally with and extending smoothly and uninterruptedly from the outer wall to an apex, said conical base wall having a convex central part on its upper surface including the apex;

a gas input including an input connector extending coaxially from an under surface of the conical base wall and a gas jet hole through the apex of the conical base wall connecting with the interior of the input connector;

a flange plate extending above said conical wall from adjacent the outer periphery of the conical base wall to the apex, the under surface of said flange plate closely matching the convex central part of the upper surface of the base wall and being spaced from said conical base wall by a sufficiently small distance to provide a capillary path from its lower outer periphery to the apex;

a reservoir for liquid being provided between said flange plate and said outer wall; and a gas/liquid jet for mixing gas from the gas jet hole through the conical base wall with liquid from the capillary path, the gas/liquid jet comprising a hole through the flange plate opposite said gas jet hole through the conical base wall, the upper surface of the flange plate extending smoothly and conically away from the gas/liquid jet;

a substantially flat annular baffle plate, including a target centrally mounted on said plate opposite said gas/liquid jet against which said gas/liquid jet impinges to nebulize the liquid;

the baffle plate intersecting the periphery of the target to provide a relatively smooth transition surface in the path of movement of the nebulized gas/liquid mixture; and, outlet aperture means adjacent the outer peripheral edge of said baffle plate for allowing direct passage of the nebulized gas/liquid mixture from the nebulizer.

In prior arrangements (seen as that shown in FIG. 1) the jet is normally mounted on a part (usually tubular) which extends axially away from the supporting transverse wall forming the base of the reservoir within the nebulizer and this has meant that the jet can move radially owing to flexure of the transverse wall. In the present arrangement, the jet is formed in the transverse wall itself and, therefore, is unlikely to move from its central position even if the wall does flex. The use of a conical wall may allow the nebulizer to be used in different orientations.

In order for the described nebulizer to contain sufficient water (because of the provision of a conical wall in place of a substantially flat transverse wall, which reduces the volume of the reservoir for a given diameter) it is necessary for the nebulizer to be somewhat wider than those generally available, but this has the added advantage of making the nebulizer more convenient to fill and also more stable when placed on a surface during the filling operation.

Nebulizers incorporating the various aspects of the invention will now be described by way of example only and with reference to the accompanying drawings in which FIG. 1 is an axial section of a known nebulizer, FIG. 2 is an axial section of a first nebulizer according to the present invention in a vertical orientation, FIG. 3 is an axial section of the first nebulizer of FIG. 2 in a horizontal orientation, FIG. 4 is a perspective view of the first nebulizer of FIG. 2, FIGS. 5, 6 and 7 are side views of the three components forming the first nebulizer of FIG. 2, FIG. 8 is an axial section of a second nebulizer according to the present invention in a vertical orientation, FIG. 9 is an axial section of a third nebulizer according to the present invention in a vertical orientation, FIG. 10 is a perspective view of part of the third nebulizer of FIG. 9, FIG. 11 is an axial section of a fourth nebulizer according to the present invention in a vertical orientation, FIG. 12 is a graph of the droplet size distribution of a nebulizer of the type shown in FIG. 1, FIG. 13 is a graph of the droplet size distribution of a nebulizer in accordance with U.S. Pat. No. 4,588,129.

FIG. 14 is a graph of the droplet size distribution of a nebulizer in accordance with U.S. Pat. No. 4,746,067, FIG. 15 is a graph of the droplet size distribution of a nebulizer according to FIGS. 2 to 7, FIG. 16 is a graph of the droplet size distribution of a nebulizer in accordance with FIG. 8, FIG. 17 is a graph of the droplet size distribution of a nebulizer in accordance with FIG. 9, FIG. 18 is a graph of the droplet size distribution of a nebulizer in accordance with FIG. 8 but modified similar to that of U.S. Pat. No. 4,588,129, that is having a rearwardly extending chamber between the target and ring.

Figure 1:
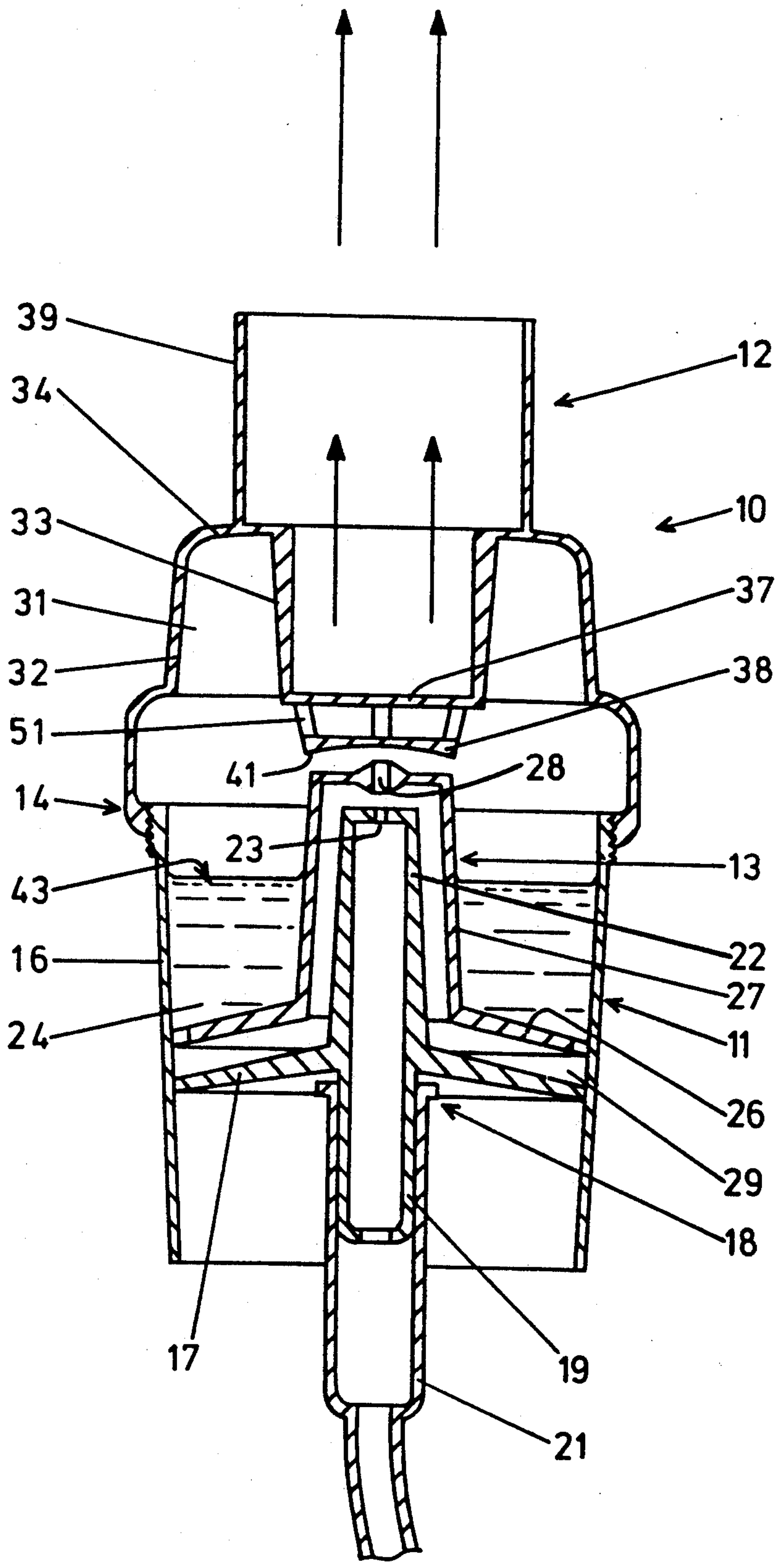

Referring now to FIG. 1 there is shown a known nebulizer 10 moulded of rigid plastics material in three separable parts, as base part 11, a cap part 12 and a flange plate 13. The base part 11 is screw threadedly engaged with the cap part 12 by means of a continuous screw thread at 14 (not shown in detail).

The base part 11 comprises a generally cylindrical outer wall 16, a transverse wall 17 extending across the lower part of the cylindrical outer wall 16 with a slight upward slope to its centre so that it comprises a shallow conical wall. Passing through the axial centre of the transverse wall 17 is the gas inlet 18, the gas inlet being defined by a gas inlet connector 19 extending downwardly from the transverse wall 17 to which a standard type gas supply tube 21 may be connected. The gas inlet 18 also extends upwardly from the transverse wall 17 by means of the extending tube portion 22, the upper end of the tube portion 22 being generally in the plane of the upper end of the cylindrical outer wall 16 and being closed by an end wall which includes an aperture therein forming a gas jet 23. It will be understood that the volume between the inner surface of the cylindrical outer wall 16 and the outer surface of the tube portion 22 forms a reservoir 24 for liquid.

The flange plate 13 comprises a shallow conical skirt portion 26 and an upright tubular part 27 extending from the skirt 26, the upper end of the tubular part 27 being closed, but including a gas/liquid mixing jet 28.

In use the configuration is such that a very narrow gap (forming a capillary path 29) is formed between the undersurface of the skirt part 26 and the upper surface of the transverse wall 17 and between the inner wall of the tubular part 27 and the outer wall of the tube portion 22 whereby liquid in the reservoir 24 may be drawn up through this capillary path 29 from the circular outer lip of the skirt part 26 within the reservoir up to the gas/liquid jet 28.

The cap part 12 comprises a screw threaded portion to engage with the base part 11, and a substantially closed cylindrical upper portion which forms a reservoir 31 for the liquid within the reservoir 24 when the nebulizer 10 is disposed horizontally. The reservoir 31 is provided between the outer cylindrical wall 32 and an inner cylindrical wall 33, the two cylindrical walls 32 and 33 being joined at their outer end by a generally transverse annular wall 34, an upstanding cylindrical portion extending from this annular wall 34 to provide an outlet connector for the gas/liquid mixture. A transverse wall 37 closes the inner end of the inner cylindrical wall 33 and mounts a baffle plate 38 which is disposed just above the gas/liquid mixing jet 28. The undersurface of the baffle plate 38 includes a shaped semicylindrical target 41 aligned with the gas/liquid mixing jet 28. Aperture means 51 is provided to allow the nebulized gas/liquid mixture to pass from within the nebulizer to the output connector 39, which may be provided by apertures in the diaphragm wall 37.

In operation, the cap part 12 is removed from the base part 11 and the necessary liquid to be nebulized is poured into the reservoir 24 up to level 43. The cap part 12 is then re-engaged with the base part 11 and the gas supply tube 21 connected to the gas inlet connector 19.

Gas may then be passed under pressure through to the gas nozzle 23 and the action of this causes liquid to be drawn up through the capillary path 29 and to be mixed with the gas and nebulized at the gas/liquid mixing jet 28. By careful design of the jet sizes and relationship with the baffle plate 38 a nebulized mixture of gas and liquid is ejected from the region of the gas/liquid mixing jet 28 and passes out to the output connector 39.

Although such a nebulizer works well, there have been a number of problems as set out in the introduction above. Thus, relative movement of the tube 21 and the nebulizer will cause the transverse wall 17 to flex very slightly and this causes movement of the gas/liquid mixing jet 28 with respect to the target 41. This movement can affect the nebulization effect.

Furthermore, the axial length of the nebulizer of FIG. 1 is considerable and it would be desirable to make a more compact arrangement.

It is difficult for old people to unscrew the cap part 12 and to fill the reservoir 24, because of its relatively small size and this is particularly important, because any spillage will affect the amount of medication being applied to the patient.

A first nebulizer according to the invention is illustrated in FIGS. 2-7. Similar parts are indicated with the same reference numerals and the general arrangement will not be described further, as it is generally similar to the nebulizer of FIG. 1.

In general terms it will be seen that the first nebulizer of the invention is considerably shorter in axial length than the nebulizer of FIG. 1 thereby making it more compact, the reservoir 31 is somewhat wider which makes it easier to fill. Other advantages will become apparent.

In the base part 11 of the nebulizer according to the invention the generally transverse wall 17 and tube portion 22 is replaced by a wall 46 which is more steeply conical than the transverse wall 17 of FIG. 1. Thus, the outer periphery of the closure wall 46 is disposed generally adjacent to the base of the cylindrical wall 16 and extends upwardly at an acute angle between 20° and 60°, preferably 45°, although with a curved central part. The gas inlet connector 19 is mounted directly in this closure wall 46 on the axis of the nebulizer. The gas inlet connector 19 extends downwardly from this central region of the closure wall 46 to a point just above the lower edge of the nebulizer. There are also provided strengthening flanges 47 which extend between the upper end of the gas inlet connector 19 and the under side of the closure wall 46 adjacent the central area.

Similarly, the flange plate 13 is shaped so as to follow the contours of the upper surface of the closure wall 46 and thereby comprises a generally conical shape, the shape of the under surface of the flange plate 13 closely matching the upper surface of the closure wall 46 to provide therebetween capillary path 29. Spacing between the cap part 12 and closure wall 46 is maintained by spacers 48 moulded to the top surface of the closure wall 46 and the under surface of flange plate 13. The gas/liquid mixing jet 28 comprises a jet passing through the axis of the flange plate 13.

The spray nozzle part also includes upwardly extending fingers 49 (3 in number) which may be more readily gripped to allow removal of the flange plate 13 from the base part 11.

Because the shape of the reservoir 24 has been changed by means of the conical lower wall of the reservoir, to maintain the same volume, the outer diameter of the cylindrical outer wall 16 must be increased from 35 mm to 42 mm.

This increase in diameter also allows changes in the cap part 12. As will be understood from FIG. 1, in order to connect with standard tubing the output connector 39 has specific dimensions and in particular, has an inner diameter of 22 mm with a specific taper. Because of the increase in diameter of the nebulizer it is now possible to arrange for the inner cylindrical wall 33 to be of 22 mm diameter and this means that this inner cylindrical wall 33 can itself form the output nozzle 39.

The baffle plate 38 and target 41 are combined with the wall 33, the target 41 comprising a divergent surface diverging away from the jet 28. The target 41 in the preferred arrangement comprises a semi spherical protrusion from the underside of the baffle plate 38. Thus the distance between the target 41 and the top surface of the flange plate 13 rapidly diverged from one another within increasing distance from the jet. It has been found that the particular arrangement of surfaces creates a very good nebulizer.

Apertures 51 are provided around the inner end of the inner cylindrical wall 33 to allow the nebulized gas liquid mixture to pass out of the interior of the nebulizer to the output connector 39. To prevent the cylindrical connector portion of the tube engaging with the output connector 39 from covering the apertures 51, the apertures 51 are provided in an inwardly extending conical inner part 52 of the cylindrical wall 33.

Instead of continuous threads being provided on the threaded portions of the base part 11 and cap part 12 there are provided interrupted thread portions which require less turning to tighten than a complete screw thread.

It will be understood that all parts of the nebulizer are moulded from the same rigid plastic which may be rigid polystyrene (styrene butadiene block copolymer).

Figure 2:
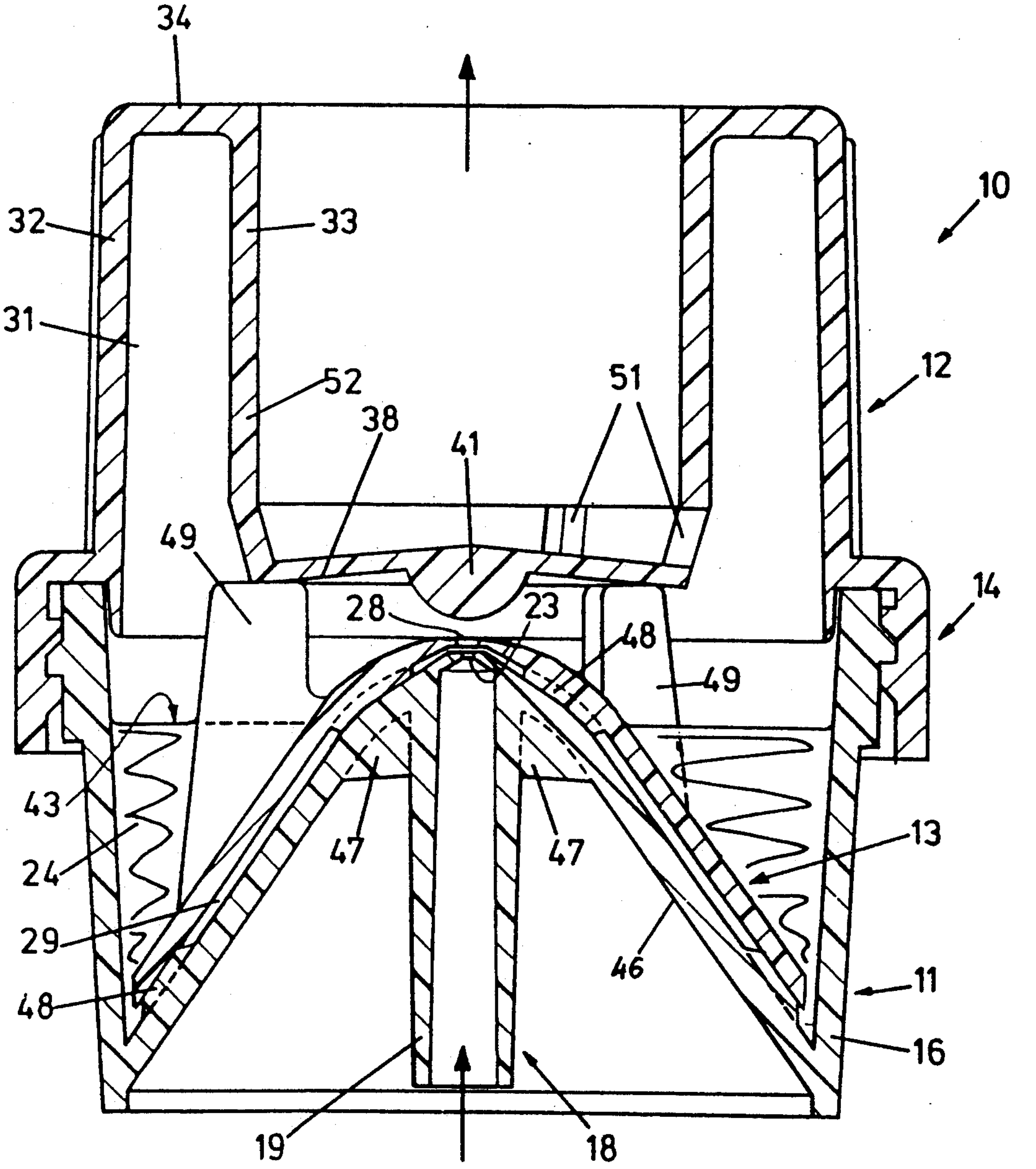

FIG. 2 shows the nebulizer according to the invention in the vertical orientation and the level of liquid within the reservoir 24 is illustrated at 43. It can be seen that this liquid level is below the gas/liquid mixing jet 28.

Figure 3:
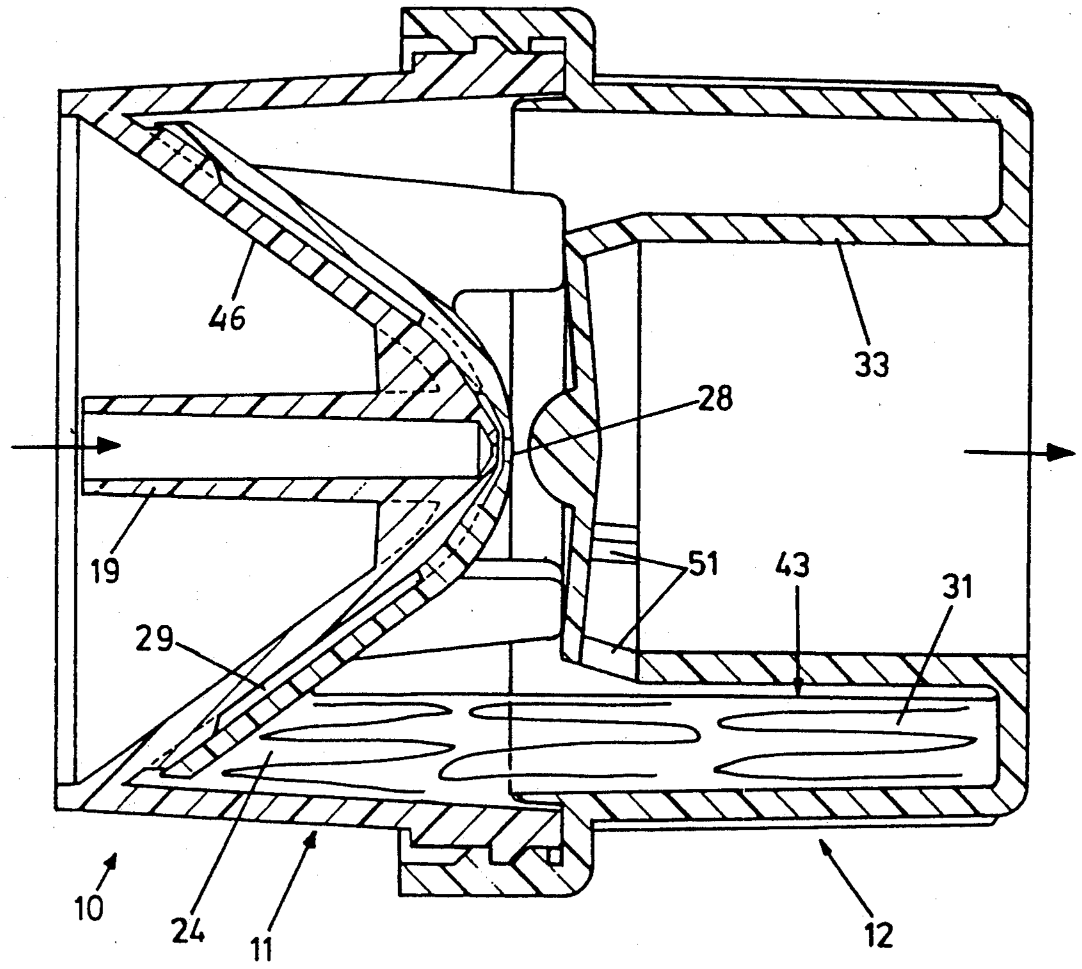
Figure 4:
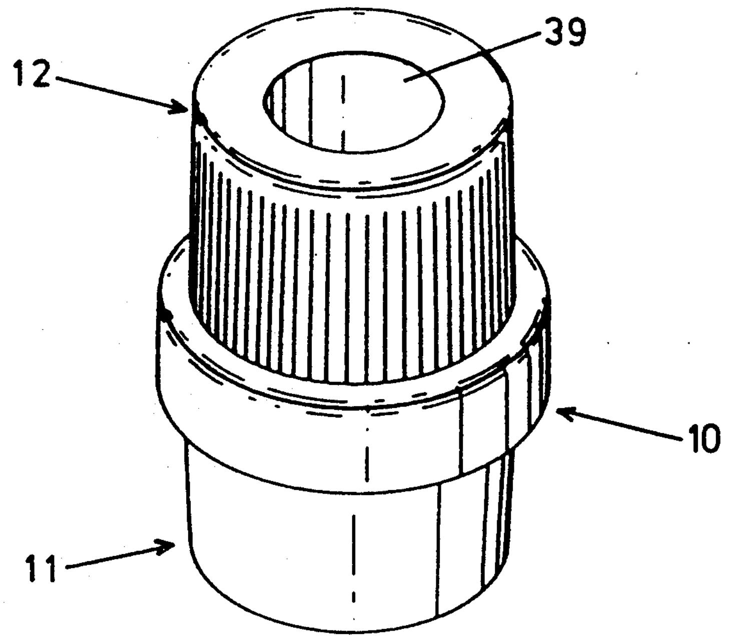
Figure 5:
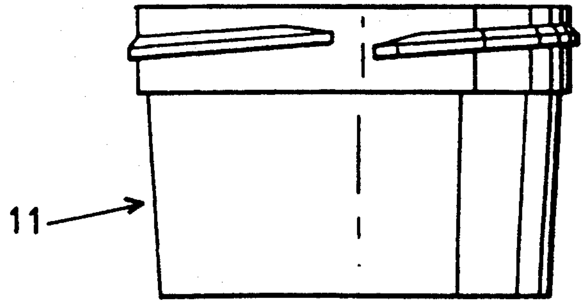
Figure 6:
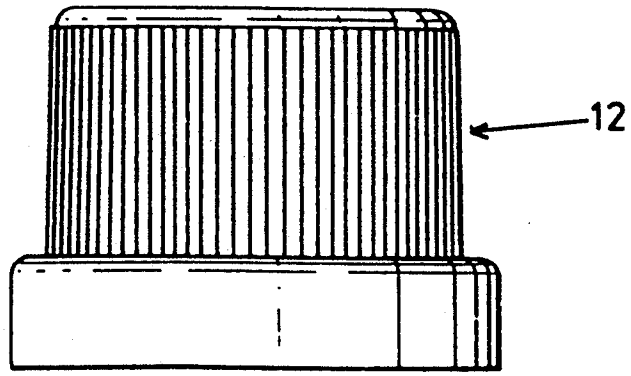
Figure 7:
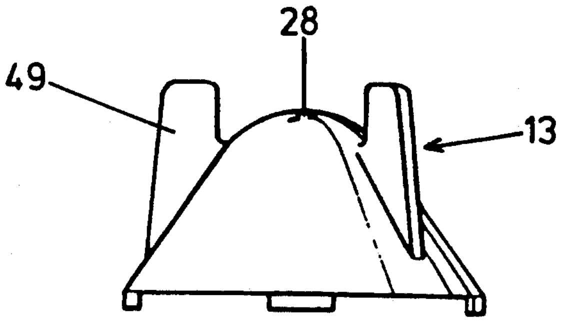

FIG. 3 shows the nebulizer when in the horizontal orientation from which it will be seen that the level of the liquid 43 (which is now distributed between the reservoir 24 and the reservoir 31 is still below the gas/liquid mixing jet 28 and the apertures 51 so that no spillage occurs. Indeed, even if the nebulizer were to be inverted completely then all of the liquid would be retained within the reservoir 31 without any spillage out of the apertures 51.

From FIG. 3 it would be seen in particular that even in the horizontal position liquid will be drawn up through the capillary 29 as the flange plate 13 extends down to the liquid.

Some of the improvements in this nebulizer will be readily apparent. The nebulizer is more compact so far as its axial length is concerned (50 mm compared with 75 mm for our earlier nebulizer of FIG. 1), because the output connector has been removed and replaced by an enlarged inner cylindrical wall 33. The elimination of the tube portion 22 means that the inner end of the gas supply tube (not shown) when engaged with the gas inlet connector 19 is now adjacent to the gas/liquid jet 28 and this further reduces the axial length as well as allowing a better form of capillary path 29 which improves the liquid flow therethrough.

To compensate for this, the nebulizer is wider and in particular the base part 11 is of greater diameter which renders it more stable when it is placed on a surface for filling. This enables easier filling of the reservoir by an elderly person and less likelihood of spillage.

The gas/liquid mixing jet 28 and gas nozzle 23 are more rigidly mounted with respect to the outer cylindrical wall 16 as they are directly connected by the conical closure wall 46. Furthermore, the attachment of the gas inlet connector 19 directly to the underside of the gas nozzle 23 means that even if that gas inlet connector 19 moves slightly, it will have very little effect on the position of the gas jet and there will not be leverage of that movement by the upwardly extending tube portion 22 of the nebulizer of FIG. 1. In any case, the flexure of the tube portion 22 and the closure wall 46 is further resisted by the flanges 47.

It is well known that the three parts of the nebulizer must be separated for regular cleaning and removal of the flange plate 13 has been particularly difficult with the arrangement of the nebulizer of FIG. 1. The increased diameter of the nebulizer and the provision of the fingers 49 simplifies removal of the flange plate 13 since these can be more readily gripped for removal thereof.

Figure 8:
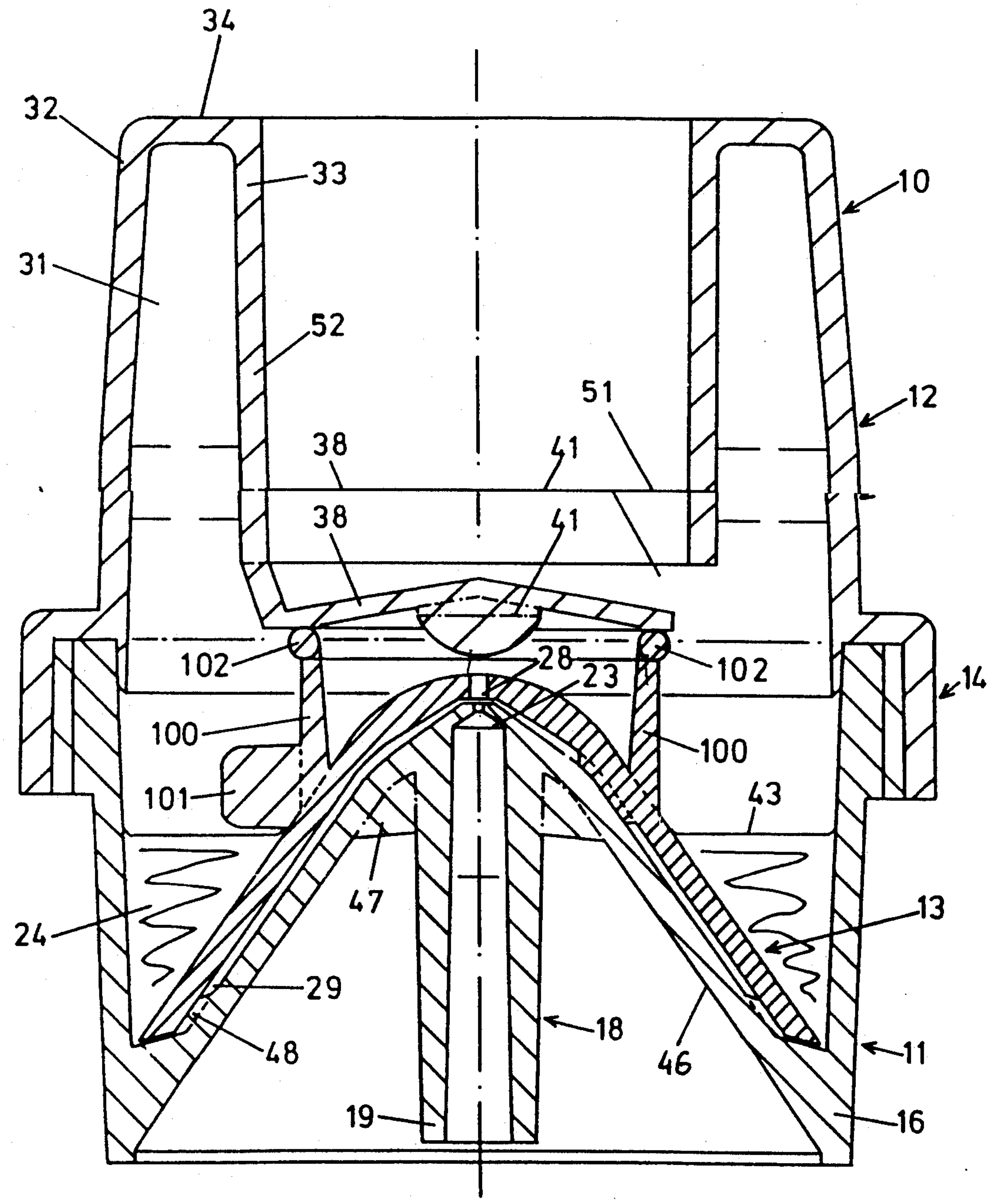
Figure 10:
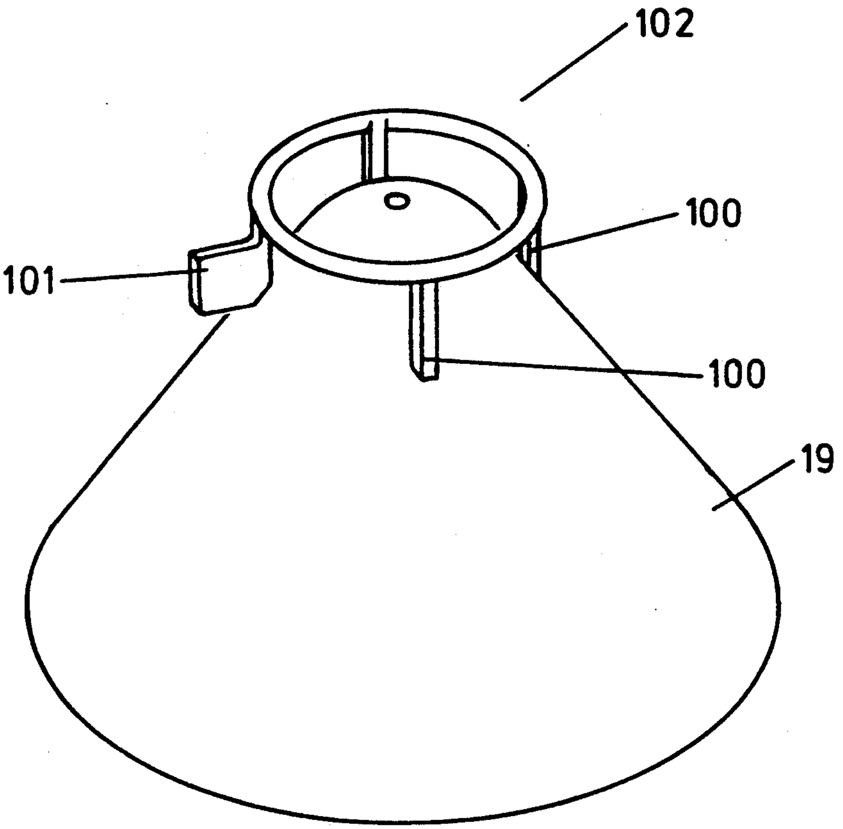

We now refer to FIG. 8. The second nebulizer described in FIG. 8 is generally similar to that of FIGS. 2 to 7 with the following changes. As can be seen from FIG. 8 (and FIG. 10 which is a perspective view of the flange plate 13 alone), the fingers 49 have been replaced by four legs 100, one of which carries a fin 101 for ease of handling, and a ring 102 joins the upper end of each leg 100. These parts may all be arranged so as to be moulded with the flange plate 13.

As can be seen from FIG. 8, the uppermost surface of the ring 102 abuts the undersurface of the baffle plate 38.

The ring 102 is of an overall diameter such that it extends substantially just inside the peripheral edge of the baffle plate 38 (the outer diameter of the baffle plate 38) being 22 mm and the diameter of the ring (overall maximum diameter) being 20 mm. In cross section, the ring is 1.6 mm wide and 1.5 mm deep.

Figure 9:
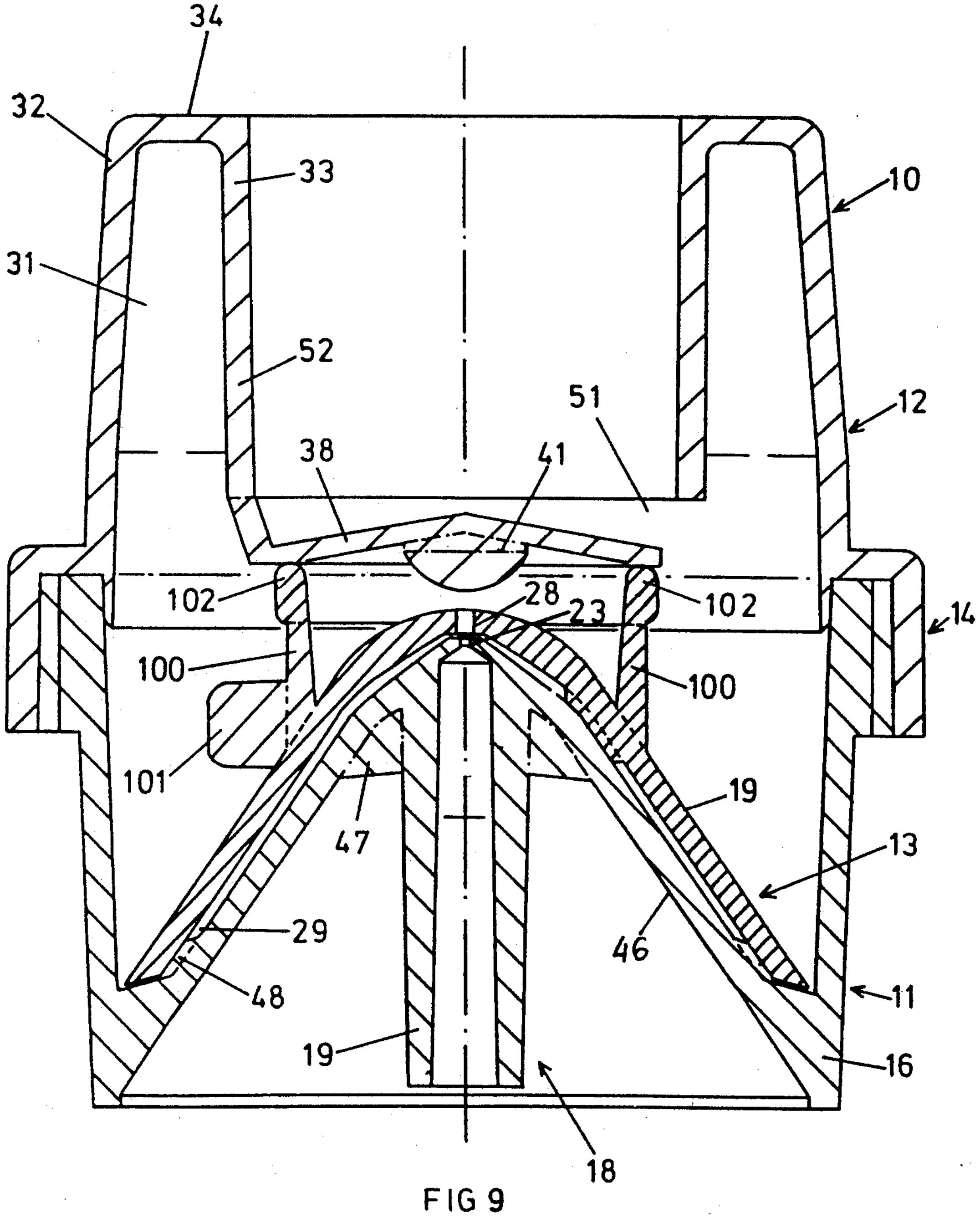

The semispherical target 41 provided in the arrangement of FIGS. 8 and 9 has a radius of 3.67 mm, and the gap between the top surface of the gas/liquid mixing jet 28 and the closest point of the surface of the target 41 is 1 mm. It will be noted from FIG. 8 that the lower edge of the ring 102 is below the lower most point of the target 41.

The arrangement of FIG. 9 is the same as FIG. 8 except that the depth of the ring is 3 mm instead of 1.5 mm. Thus the lower most edge of the ring 102 is even further below the lower most point of the target 41 than in FIG. 8.

In FIGS. 8 and 9, the ring 102, because it abuts the baffle plate 38 effectively forms a downwardly directed baffle or skirt.

Figure 11:
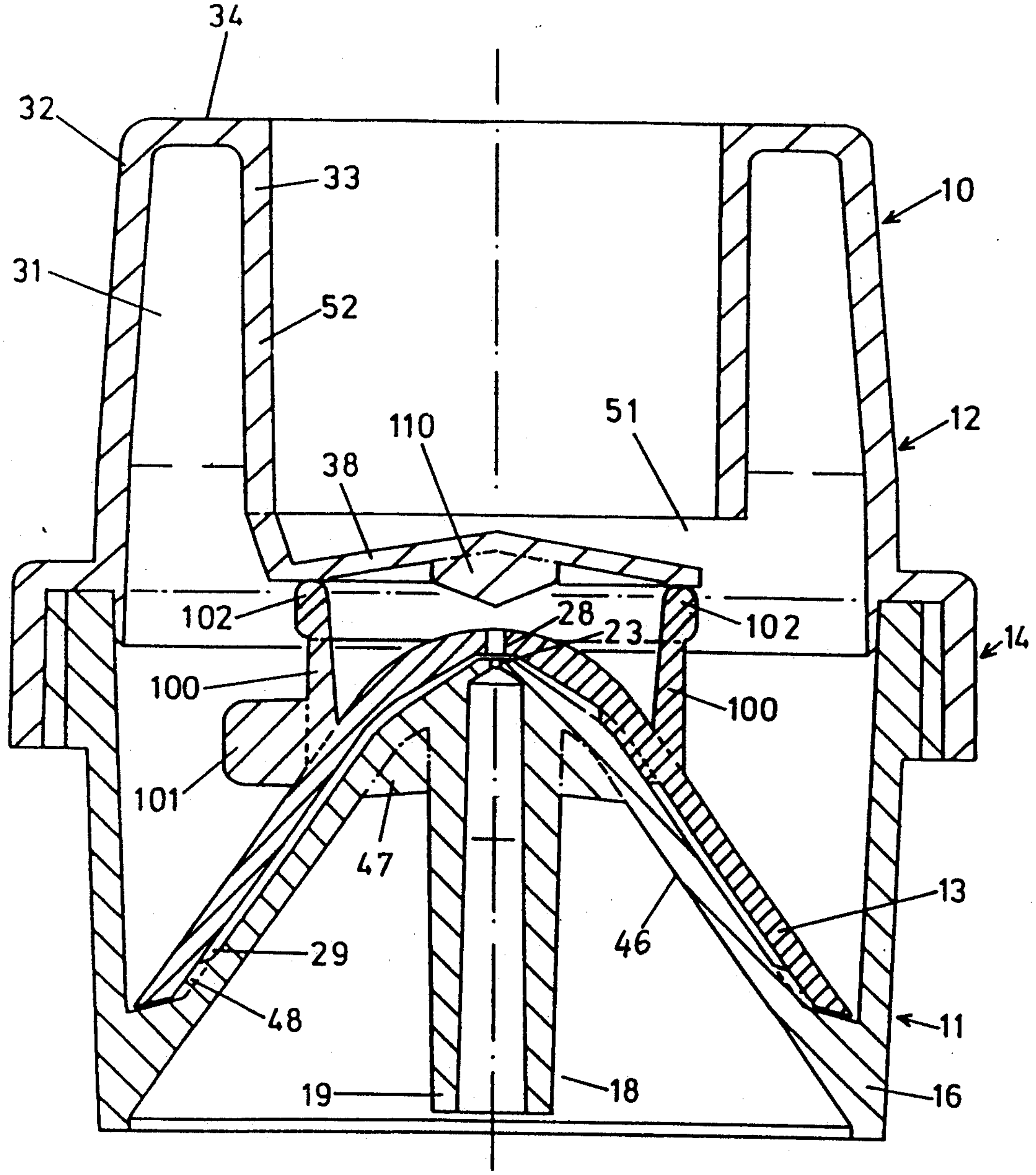

We also refer to FIG. 11. This corresponds to FIG. 8 except in place of the semispherical target 41 there is provided, a conical target 110. The angle of the surface of the conical target 110 with respect to its axis is between 55 degrees and 80 degrees, preferably 70 degrees.

As mentioned above, it is desirable to be able to produce nebulized droplets of a desired size range and a droplet size (i.e. diameter) of less than 8 micron is desirable and for many purposes (although not all), a droplet size of less than 3.5 micron is desirable and between 0.5 and 2.5 micron is particularly desirable.

Of course, in practice, there is a range of droplet sizes produced and it is desirable to be able to provide, for a particular nebulizer in use, a measure of the spread of droplet sizes and a mass median diameter (MMD).

FIGS. 12 to 19 show test results analysing the droplet size distribution for a variety of nebulizers. These graphs have been produced by the use of a Malvern 2600C droplet size analyser manufactured by Malvern Instruments of Spring Lane South, Malvern, United Kingdom.

The Malvern 2600C is a laser diffraction device. To measure droplet size, a beam of laser radiation is shone through the droplets from the nebulizer. The smaller droplets diffract the laser light (i.e. divert the laser light) at a larger angle and the larger droplets divert the light at a smaller angle. The light is focused by a lens on to a detector and the light intensity pattern on the detector is analysed by a computer. The computer then gives a volume distribution of variously sized droplets.

The nebulizer droplets cannot be counted to give a number distribution, because there are too many droplets for the computer to handle, and a number distribution would be uninformative. Importantly, a number distribution is misleading because a large number of nebulized small droplets can account for only a very small volume of drug solution nebulized, since volume is proportional to radius cubed.

A histogram of the volume distribution provides an easily discernable distribution of the droplet size against the quantity of drug.

The graphs in FIGS. 12 to 19, therefore, show volume distribution against droplet size for various nebulizers. They were all carried out under the same conditions, viz dry compressed air was passed through the nebulizer at 8 liters a minute and the nebuliser reservoir contained water.

The droplet size scale is a logarithmic scale extending between 1 and 100 micron. As can been seen the graph has two parts, a line graph and a histogram. The left-hand vertical scale relates to the line graph. The left-hand scale is of the percentage of the total volume of droplets below the relevant droplet size. The righthand scale which relates to the histogram is a scale of percentage of the total volume of droplets which are of a droplet size within the limits set by the width of the relevant bar of the histogram.

There is also provided with each graph a figure for the mass median diameter (MMD). There is also provided with each graph a figure for the mass median diameter (MMD). This is the diameter above which 50% of the volume of droplets lie and below which a further half lies. This, combined with the Geometric Standard Deviation gives an indication of the quality of the aerosol produced.

The GSD is a mathematical figure and is a good way of comparing the spread of various droplet distributions. If the GSD is large there is a large range of droplet sizes; if the GSD is small the particles are of similar sizes and the sizes are clustered around the MMD. An aerosol may be considered to be monodispersed if the figure is under 1.22, and heterodispersed above that figure.

For the nebulizer to efficiently provide drug through to the alveoli of the lung, it is desirable that the mass median diameter (MMD) should be about 1.25 micron with a geometric standard deviation of about 0.7 effectively reasting a monodispersed aerosol.

Figure 12:
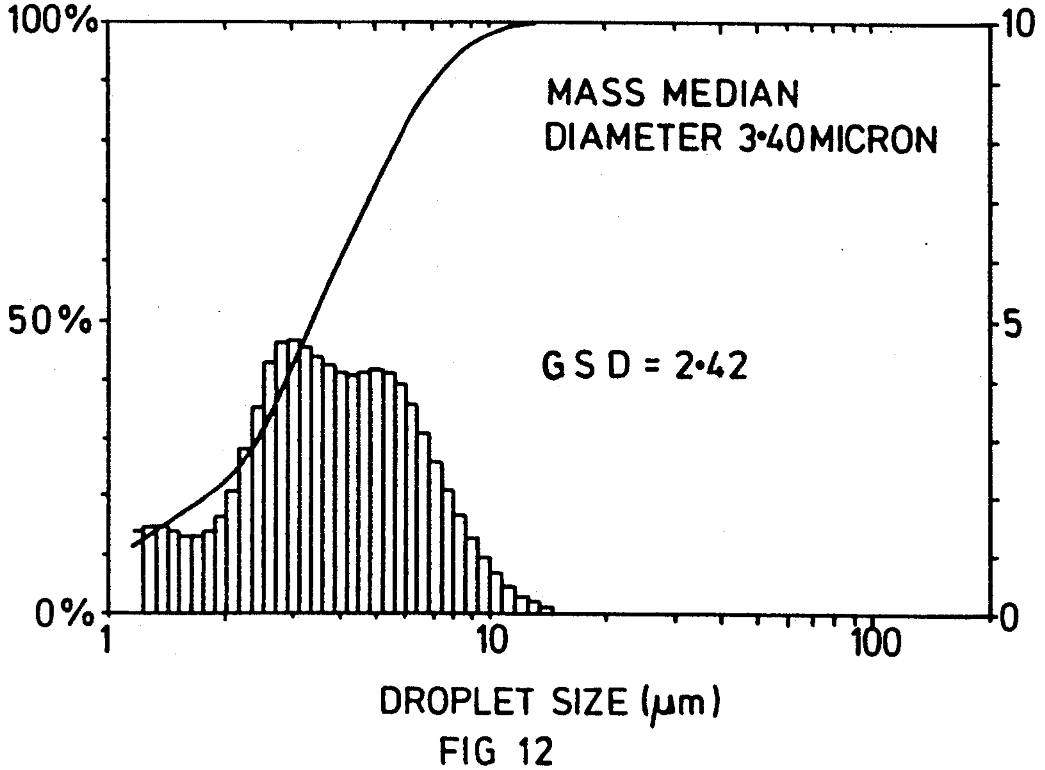

FIG. 12 shows the droplet size distribution for a nebulizer in accordance with FIG. 1. As can be seen, there are relatively few droplets in the range 1-2 micron, and there are a number of droplets going up beyond 10 micron. The mass median diameter (MMD) is 3.4 micron with a geometric standard deviation of 2.42. As a result few droplets will be of a size to reach the alveoli.

Figure 13:
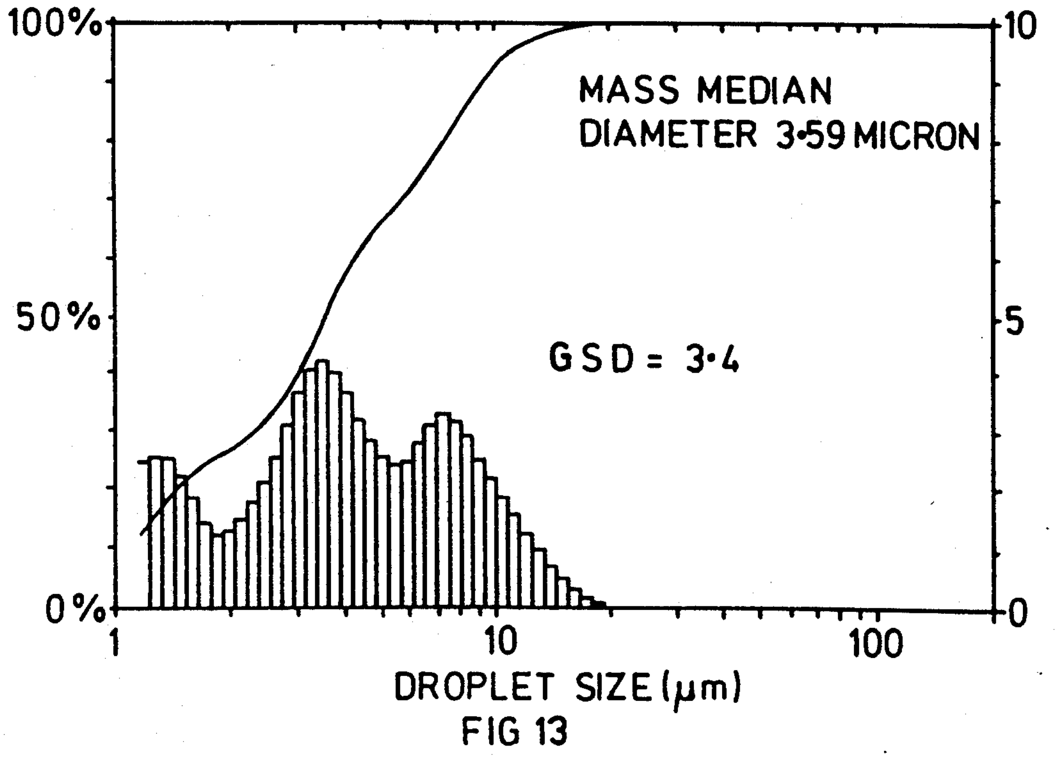

The applicants have obtained a nebulizer made in accordance with U.S. Pat. No. 4,588,129 and FIG. 13 illustrates the droplet distribution of that nebulizer. As will be understood from that U.S. Pat. No. 4.588,129, there is some discussion of the value of the droplet size. It will be seen that the measured droplet distribution provides a volume distribution in which the bulk of droplets are approximately 3.5 micron in diameter, and the mean diameter is in fact measured to be 3.59 micron with a geometric standard deviation of 3.4.

Figure 14:
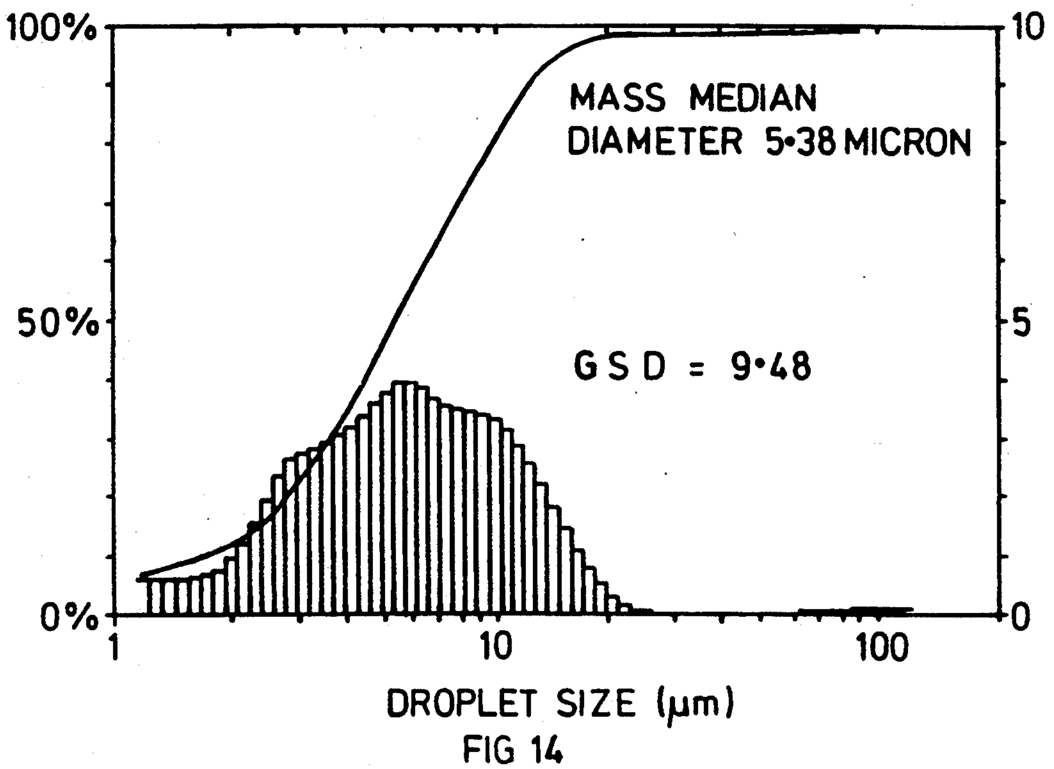

FIG. 14 shows the droplet size distribution for a nebulizer made in accordance with U.S. Pat. No. 4,746,067. A somewhat similar distribution is provided to that of FIG. 13 but the mass median diameter (MMD) is greater at 5.38 micron with a geometric standard deviation of 9.48. This is a particularly high figure because there are some particles in the 100 micron range. Once again, few droplets would reach the alveoli.

Figure 15:
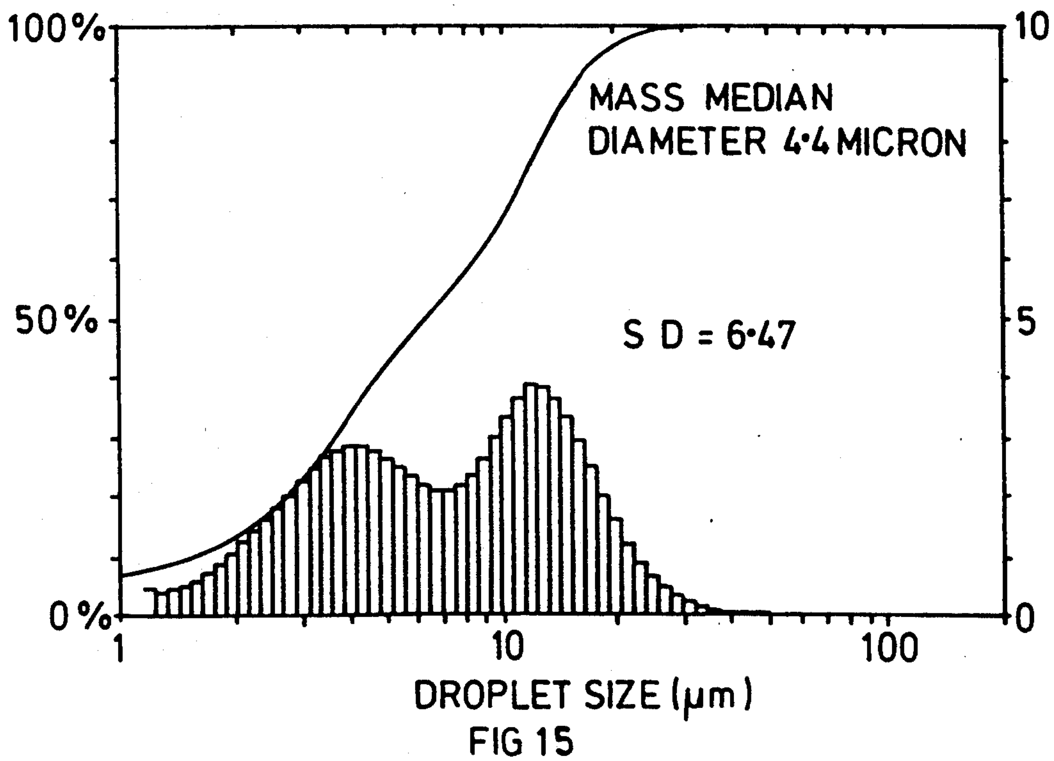

FIG. 15 shows the droplet size distribution for a nebulizer in accordance with FIGS. 2-7. The mass median diameter (MMD) 6.44 micron with a geometric standard duration of 6.47.

Figure 16:
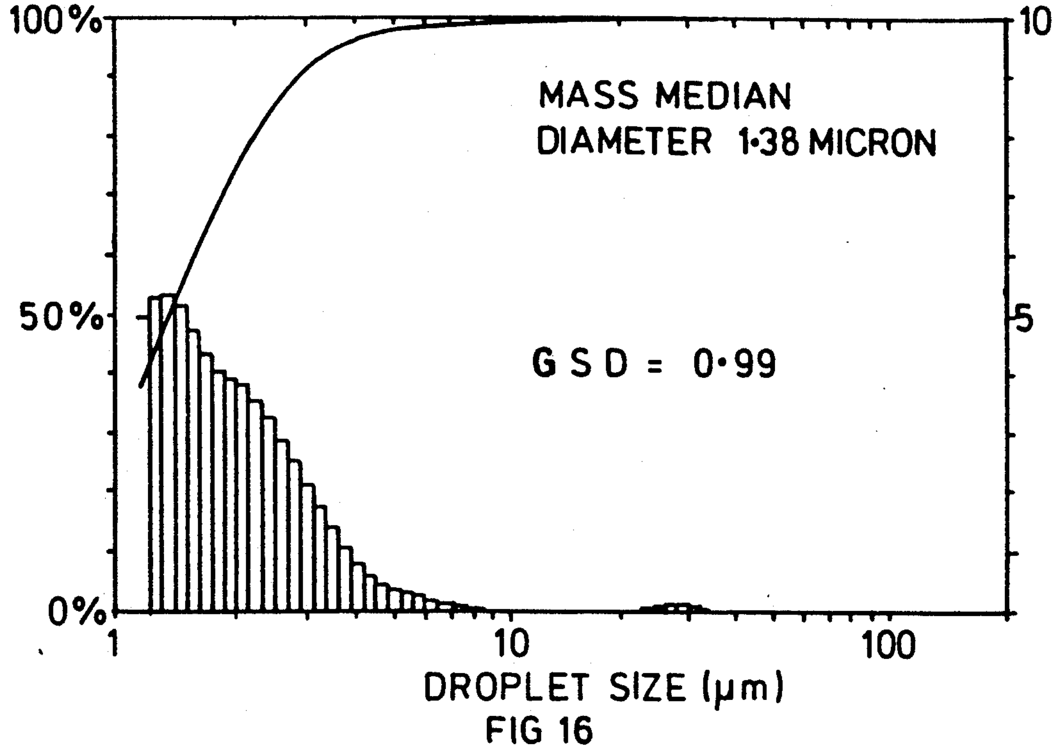

FIG. 16 shows the droplet size distribution for a nebulizer of the type shown in FIG. 8. It will be immediately seen that there is a dramatic improvement in the distribution, very many more droplets being of a smaller size and indeed virtually no droplets being of a size greater than about 8 micron. The mass median diameter (MMD) is 1.38 micron with a geometric standard deviation of 0.99. As a result a large proportion of the droplets would pass the alveoli.

Figure 17:
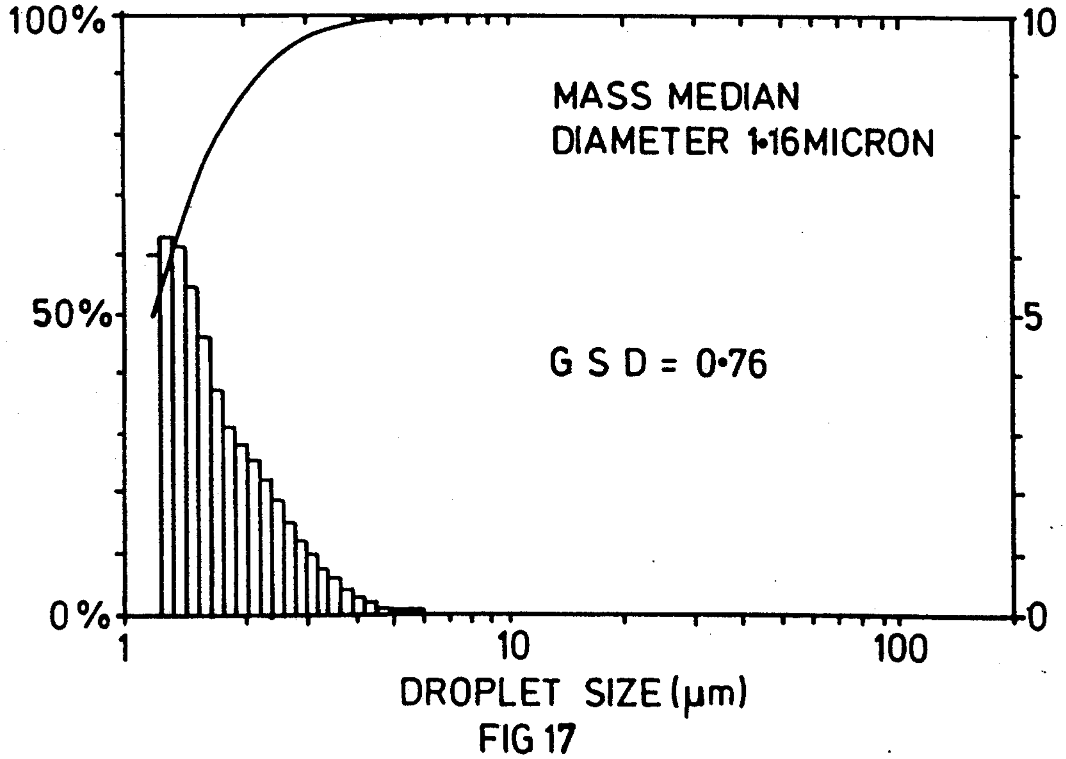

FIG. 17 shows the droplet size distribution for the nebulizer of FIG. 9, that is with a deeper ring. This shows a reasonable improvement upon the arrangement of FIG. 16, the mass median diameter (MMD) now being 1.16 with a geometric standard deviation of 0.76, the improvement in the very small size droplets being particularly great. Once again, the bulk of the droplets would pass to the alveoli.

Figure 18:
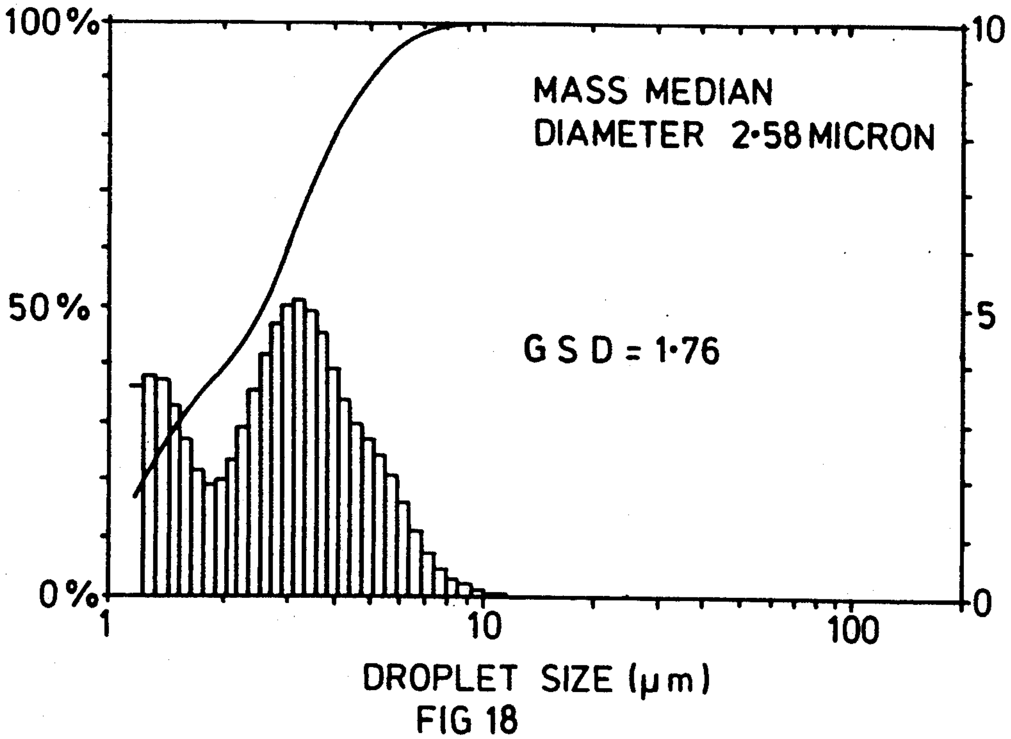

FIG. 18 is a graph of the droplet size distribution of a nebulizer in accordance with FIG. 8 but modified similar to that of U.S. Pat. No. 4,588,129, by having a rearwardly extending chamber between the target 41 and ring 100. It can be seen that this makes the situation considerably worse, reducing the number of small droplets considerably, and providing a peak at about 3 micron. As a consequence the mass median diameter (MMD) increases to 2.58 micron with a geometric standard deviation of 1.76.

Figure 19:
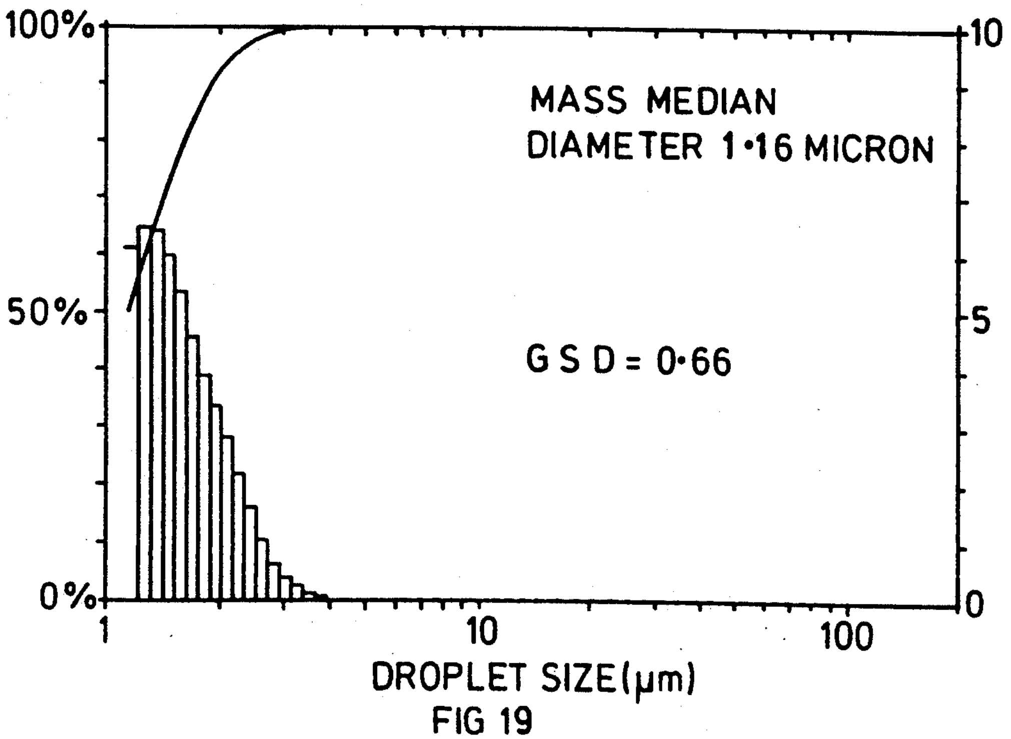
FIG. 19 is a graph of the droplet size distribution of a nebulizer according to FIG. 11.

FIG. 19 is a graph of the droplet size distribution of a nebulizer according to FIG. 11, that is with a conical target 41. There is a very good droplet size distribution, generally corresponding to that of FIG. 17, providing a large number of very small droplets and no droplets about 4 micron. The mass median diameter (MMD) is 1.16 micron and the geometric standard duration has dropped to 0.66, a very good figure.

It will be seen therefore that the provision of the ring 102 dramatically improves the situation with regard to the droplet size distribution.

Figure 20:
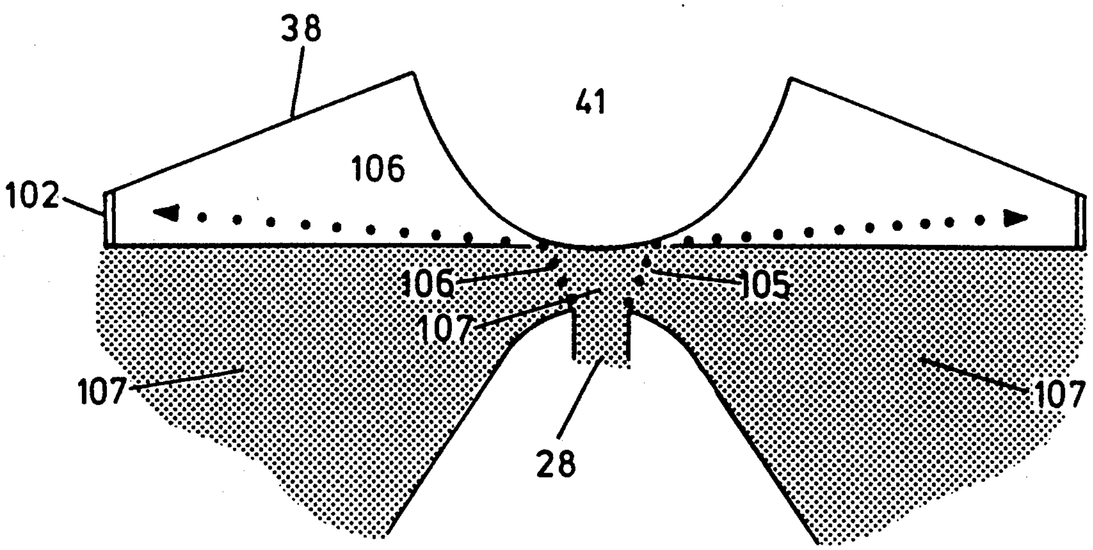
FIG. 20 shows a diagrammatic view of the nebulized jet of gas/liquid and the path of said gas/liquid jet.

As a result of experimentation, we believe (although in no sense should the present invention be restricted as a result of this theory) that the gas/liquid jet 28 provides a cone 105 of nebulized gas/air mixture (see FIG. 20), in which the periphery 106 of the cone 105 includes droplets of larger size. This conical jet 105 impinges upon the target 41 and in the arrangement of FIGS. 8 to 11, is then deflected and the ring 102 is disposed so as to collect the outer peripheral 106 part of the cone of nebulized gas/liquid (see FIG. 20). As a result the smaller droplets (at 107) which are concentrated in the middle of the cone pass out of the nebulizer and the larger droplets are trapped.

As a result of considerable experimentation, we believe that a number of factors affect the size of the droplets provided by the nebulizer.

We also believe that the disposition of the lower edge of the ring, which effectively forms a skirt surrounding the target 41, is of importance. Indeed, we believe that the nebulizer works more effectively because the lower edge of the ring is below the lower most point of the target 41.

The provision of the relatively flat plate 38 extending between the target 41 and the ring 102 is clearly important. Thus the difference between the results shown in FIG. 15 and that of FIG. 17, wherein the only difference is that the relatively flat plate 38 has been replaced by a chamber as in U.S. Pat. No. 4,588,129 suggests that this relatively flat plate is important.

It will be understood from the above that it is possible to provide interchangeable parts to provide droplet size characteristics required. For example, by simply interchanging the flange plate 13 of FIGS. 2-7 with the flange plate of FIG. 8, one can change the characteristics of the nebulizer so as to produce a mass median diameter (MMD) which changes from 6.44 micron to 1.38 micron for different purposes.

The invention is not restricted to the details of the foregoing examples.

I claim:

1. A nebulizer comprising:

a base part including a base wall extending to an apex;

a gas input including an input connector;

a gas jet hole extending through the base wall connecting with the interior of the input connector;

a gas/liquid output;

a flange plate extending above said base wall over the gas jet hole, the under surface of said flange plate generally matching the upper surface of the base wall and being spaced from said base wall by a sufficiently small distance to provide a capillary path;

a reservoir for liquid being provided by said base wall communicating with said capillary path; and, a gas/liquid mixing jet for mixing gas from the gas jet hole through the base wall with liquid from the capillary path to produce an aerosol of liquid droplets having a wide range of sizes, the gas/liquid mixing jet comprising a hole through the flange plate opposite and in axial alignment with said gas jet hole through the base wall; and means for removing a substantial portion of the droplets greater than approximately 2 microns, including a generally flat annular baffle plate, including a target having a lowest point in the form of a protuberance from said baffle plate and centrally mounted thereon opposite said gas/liquid mixing jet against which the aerosol of liquid droplets formed by the gas/liquid mixing jet impinges to further break up some of the liquid droplets, and a ring member having a lower edge is positioned to extend downwardly from the surface of the annular baffle plate, and being generally coaxial with the target to trap larger droplets, wherein said lower edge of said ring extends below the lowest point of said target, and, outlet aperture means adjacent the outer peripheral edge of said baffle plate for allowing direct passage of the nebulized gas/liquid mixture from the nebulizer.

2. A nebulizer as claimed in claim 1 in which the lower most edge of the ring means extends below the lower most point of the target.

3. A nebulizer as claimed in claim 1 in which the target is semispherical.

4. A nebulizer has claimed in claim 3 in which the radius of the target is 2-5 mm, preferably substantially 3.5 mm.

5. A nebulizer as claimed in claim 1 in which the diameter of the ring means is 15-25 mm, preferably approximately 20 mm diameter.

6. A nebulizer as claimed in claim 1 in which the depth of the cross section of the ring means is 1–5 mm, preferably 1.5 mm.

7. A nebulizer as claimed in claim 1 in which the depth of the cross section of the ring means is approximately 3 mm.

8. A nebulizer as claimed in claim 1 in which the target comprises a conical member.

9. A nebulizer as claimed in claim 8 in which the angle of the surface of the conical target with respect to its axis is between 55 degrees and 80 degrees.

10. A nebulizer as claimed in claim 8 in which the angle of the surface of the conical target with respect to its axis is approximately 70 degrees.

11. A nebulizer as claimed in claim 1 in which the ring means is mounted by leg means, to the flange plate.

12. A nebulizer as claimed in claim 1 in which the base part comprises an outer wall and the base wall comprises a conical base wall formed integrally with and extending from the outer wall to an apex, the outer surface of said base wall having a convex central portion including the apex.

13. A nebulizer as claimed in claim 1 in which a wall of the reservoir itself forms the gas/liquid output for the nebulized gas and liquid mixture.

14. A nebulizer as claimed in claim 1 in which a cover is provided for said reservoir, said cover incorporating said gas/liquid outlet.

15. A nebulizer as claimed in claim 1 in which said reservoir includes a cover, said cover including said annular baffle plate.

* * * * *